United States Patent
Oskam

(10) Patent No.: US 10,383,712 B2
(45) Date of Patent: Aug. 20, 2019

(54) PLANNING A REPAIR OR ADJUSTMENT OF A DENTAL PARTIAL PROTHESIS

(71) Applicant: DENTSPLY SIRONA inc., York, PA (US)

(72) Inventor: Thomas Oskam, Schaffhausen (CH)

(73) Assignee: DENTSPLY SIRONA INC., York, PA (US)

(*) Notice: Subject to any disclaimer, the term of this patent is extended or adjusted under 35 U.S.C. 154(b) by 102 days.

(21) Appl. No.: 15/743,708

(22) PCT Filed: Jul. 20, 2016

(86) PCT No.: PCT/EP2016/067228
§ 371 (c)(1),
(2) Date: Jan. 11, 2018

(87) PCT Pub. No.: WO2017/013142
PCT Pub. Date: Jan. 26, 2017

(65) Prior Publication Data
US 2018/0193117 A1    Jul. 12, 2018

(30) Foreign Application Priority Data
Jul. 21, 2015 (DE) .................. 10 2015 213 682

(51) Int. Cl.
*A61C 13/00* (2006.01)
*A61C 13/01* (2006.01)
(Continued)

(52) U.S. Cl.
CPC ...... *A61C 13/0004* (2013.01); *A61C 13/0024* (2013.01); *A61C 13/01* (2013.01)

(58) Field of Classification Search
CPC ...... G05B 19/4099; G05B 2219/36248; G05B 2219/45244; G06F 19/00; G06F 19/321;
(Continued)

(56) References Cited

U.S. PATENT DOCUMENTS

| 7,758,345 B1* | 7/2010 | Christensen | ............. A61C 9/00 433/214 |
| 2007/0141531 A1* | 6/2007 | De Clerk | ............. A61C 8/0001 433/173 |

(Continued)

FOREIGN PATENT DOCUMENTS

| DE | 102007032291 A1 | 1/2009 |
| DE | 102006044215 B4 | 2/2014 |
| GB | 2496981 A | 5/2013 |

OTHER PUBLICATIONS

International Search Report and Written Opinion of International Application No. PCT/EP2016/067228 dated Oct. 14, 2016 (English translation).

(Continued)

*Primary Examiner* — Michael J Brown
(74) *Attorney, Agent, or Firm* — Dentsply Sirona Inc.

(57) ABSTRACT

The invention relates to a method for computer-aided planning of a repair or adjustment of a dental partial prosthesis with the following method steps: generation of a first digital 3D model of a jaw with the partial prosthesis positioned on the jaw as a prosthesis reference model (M1), generation of a second digital 3D model of the jaw, without the partial prosthesis, as a jaw model (M2), determination of a positional relationship of the prosthesis reference model (M1) to the jaw model (M2), generation of a digital prosthesis model (P) by subtracting the jaw model (M2) from the prosthesis reference model (M2) while taking the positional relationship into account, automatic identification and/or identification carried out by a user of holding and/or support elements in the prosthesis model (P), calculation of an insertion axis of the partial prosthesis on the basis of the prosthesis model (P), calculation of undercut depths, resulting from the insertion axis, of the holding and/or support elements in the prosthesis model (P), display of the insertion (Continued)

axis and the undercut depths in the presentation of the jaw model (M2).

8 Claims, 2 Drawing Sheets

(51) Int. Cl.
    *G05B 19/40*         (2006.01)
    *G06F 19/00*         (2018.01)
    *G06F 17/50*         (2006.01)
    *B33Y 80/00*         (2015.01)

(58) Field of Classification Search
    CPC . G06F 17/5086; B33Y 80/00; A61C 13/0004; A61C 13/0001; A61C 13/0013; A61C 9/004; A61C 8/0009; A61C 1/084; A61C 13/0024; A61C 13/01
    USPC .................................. 700/98; 433/74, 173
    See application file for complete search history.

(56) References Cited

U.S. PATENT DOCUMENTS

| | | |
|---|---|---|
| 2008/0261165 A1 | 10/2008 | Steingart et al. |
| 2011/0276159 A1 | 11/2011 | Chun et al. |
| 2012/0290118 A1 | 11/2012 | Kaigler, Sr. |
| 2013/0110469 A1* | 5/2013 | Kopelman .............. G06T 19/20 703/1 |
| 2014/0080094 A1 | 3/2014 | Howe |

OTHER PUBLICATIONS

International Preliminary Report on Patentability of International Application No. PCT/EP2016/067228 dated Jan. 23, 2018 (English translation).

\* cited by examiner

PLANNING A REPAIR OR ADJUSTMENT OF A DENTAL PARTIAL PROTHESIS

TECHNICAL FIELD

The invention relates to a method for digital planning of a repair or adjustment of a dental partial prosthesis.

BACKGROUND OF THE INVENTION

A typical task of a dental laboratory is, in addition to the creation of dental prostheses, the repair of defective dental prostheses or adding to an existing dental prosthesis, for example, by servicing new defects in a jaw. A typical case is the replacement of one or more broken brackets in a model casting. The complication in this case is, in particular, the subsequent estimation of the original insertion axis of the partial prosthesis. This step is, however, necessary both for repairs as well as for supplemental work in order to guarantee a correct undercut depth for already existing brackets and for added brackets and/or areas, and to ensure that parts, like counter brackets and guide brackets, do not have any undercut depths.

The object of the present invention is to refine the prior art and to provide a simple and reliable method to repair or adjust dental partial prostheses.

SUMMARY OF THE INVENTION

The subject matter of the invention is a method for the computer-aided planning of a repair or adjustment of a dental partial prosthesis with the following method steps: generation of a first digital 3D model of a jaw with the partial prosthesis positioned on the jaw as a prosthesis reference model; generation of a second 3D model of the jaw, without the partial prosthesis, as a jaw model; determination of a positional relationship of the prosthesis reference model to the jaw model; generation of a digital prosthesis model by subtracting the jaw model from the prosthesis reference model while taking the positional relationship into account; automatic identification and/or identification carried out by a user of holding and/or support elements in the prosthesis model; calculation of an insertion axis of the partial prosthesis on the basis of the prosthesis model; calculation of undercut depths, resulting from the insertion axis, of the holding and/or support elements of the partial prosthesis; display of the insertion axis and the undercut depths in the presentation of the jaw model.

A dental partial prosthesis consists of a framework comprising a base, e.g. a sublingual or a transverse strip, and holding and support elements, such as brackets. A prosthetic saddle and artificial teeth are fixed on the framework.

The digital 3D models of the jaw with and without the partial prosthesis may be generated by means of a scan, e.g. a scan of a plaster model generated by means of an impression of the jaw, or a direct scan of the jaw by means of an intraoral camera operating according to the triangulation method.

From the data provided by this means or from the prosthesis model calculated herefrom, it is possible to determine an insertion axis which takes into account the shape of the partial prosthesis and the position of the holding and support elements, and thus corresponds at least approximately to the insertion axis originally conceived of for the partial prosthesis.

The display and the automatic adjustment of the displayed undercut depths when changing the insertion axis facilitate a simple and continuous monitoring of the undercut depths and of the occurrence of undercut depths during changes to the insertion axis by the user. Furthermore, it is ensured by the display and adjustment of the undercut depths that the additional holding and support elements generate the desired tensile force when they are added.

Advantageously, the proposed insertion axis is changed by a user by means of an input means, and the undercut depths are automatically recalculated, thus, the user has all important criteria directly at a glance, and may quickly and easily estimate and determine a correct insertion axis.

Advantageously, the jaw model is blocked out while taking the insertion axis into account, and the prosthesis model is set on the blocked out jaw model, and supplemented or changed by a user by means of an input means. Thus, both direct monitoring during design and also the subsequent, easy, and direct computer-supported production of the parts to be added or the areas of the partial prosthesis are possible.

Advantageously, a third digital 3D model of a lower side of the partial prosthesis is generated and a lower side of the prosthesis model is added to and/or replaced by the third digital 3D model so that the prosthesis model conforms most precisely with the actual partial prosthesis.

Advantageously, prior to and/or after the calculation of the insertion axis and the undercut depths, areas to be monitored are marked automatically in a presentation of the jaw model and/or marked by means of an input means, wherein the calculation of the undercut depths for these areas is carried out and displayed so that a simple and reliable monitoring of the undercut depths is possible, for example, for holding and support elements to be newly placed or for other parts to be added to the partial prosthesis.

Advantageously, areas for holding and support elements to be added are marked on the jaw model prior to the calculation of the insertion axis and taken into account during the calculation of the insertion axis. If it is already previously known how or where the new holding and support elements, or the holding and support elements to be added, are to extend, then the result of the calculation of the insertion axis may be improved by the marking of these areas and taking these areas into account.

Advantageously, the undercut depths are visualized by coloring the surface of the jaw model in false colors so that they are easily and directly perceivable by the user.

Advantageously, areas that may cause possible wedging are determined on the basis of the prosthesis model, the jaw model, and the insertion axis, and displayed in the jaw model. Wedging may be at least estimated on the basis of the jaw model and the prosthesis model, and may be displayed to the user as a warning, for example, by color highlighting of the corresponding surface areas of the jaw model.

DETAILED DESCRIPTION OF THE INVENTION

Figure 1:
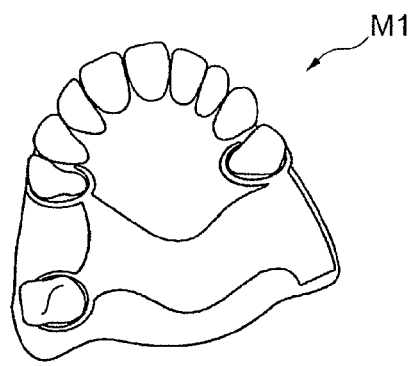
FIG. 1 a first digital 3D model of a jaw with a positioned partial prosthesis, FIG. 2 a second digital 3D model of a jaw without a positioned partial prosthesis, FIG. 3 a prosthesis model, FIG. 4 a display of undercut depths and an insertion axis within a digital 3D model of the jaw.
Figure 2:
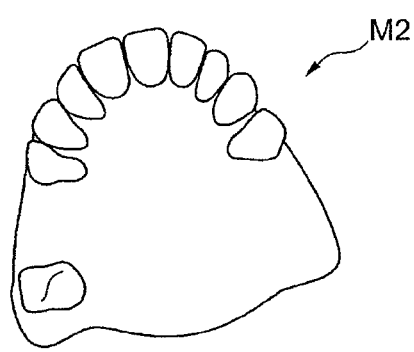

FIGS. 1 to 4 schematically visualize the method according to the invention. FIG. 1 shows a first digital 3D model which is generated by scanning a jaw or a plaster model generated by means of an impression of the jaw with a partial prosthesis positioned thereon and is stored as prosthesis reference model M1. A second 3D model is sketched in FIG. 2, which shows the jaw without the partial prosthesis, likewise generated by means of a corresponding scan and stored as jaw model M2.

Subsequently, a positional relationship is determined between prosthesis reference model M1 and jaw model M2. This may be carried out, for example, automatically on the basis of coincident areas, which are identified by means of known algorithms. In particular, if the overlapping areas are not sufficient for automatic determination of the positional relationship, the positional relationship may be determined partially or completely manually.

By subtracting 3D model M2 from M1, arranged aligned with one another, a prosthesis model P is calculated (FIG. 3), which has an upper side of the partial prosthesis contained in prosthesis reference model M1 as upper side 1. A lower side 2 of prosthesis model P, which results from the subtraction, corresponds only approximately to a lower side of the prosthesis, as not all information for this are contained in prosthesis reference model M1 and jaw model M2. Optionally, a third digital 3D model M3 may be generated by means of a scan of the lower side of the partial prosthesis, and lower side 2 of prosthesis model P may be replaced or supplemented by this data (not shown).

Figure 3:
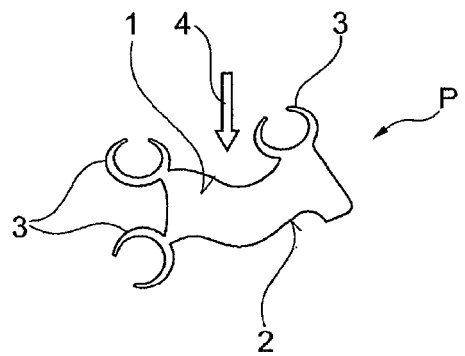

As is sketched in FIG. 3, prosthesis model P is also displayed to a user so that said user may use an input means to mark holding and support elements 3, e.g. brackets, by means of an input means (not depicted), or may confirm or correct positions of automatically detected holding and support elements 3.

A possible insertion axis 4 is subsequently automatically determined on the basis of prosthesis model P and holding and support elements 3 detected therein, and displayed to the user, for example, by means of an arrow, as shown in FIG. 3. "Possible" with respect to insertion axis 4 means that the proposed insertion axis 4 satisfies previously-stored boundary conditions with respect to undercut depths of holding and support elements 3 to be considered.

Figure 4:
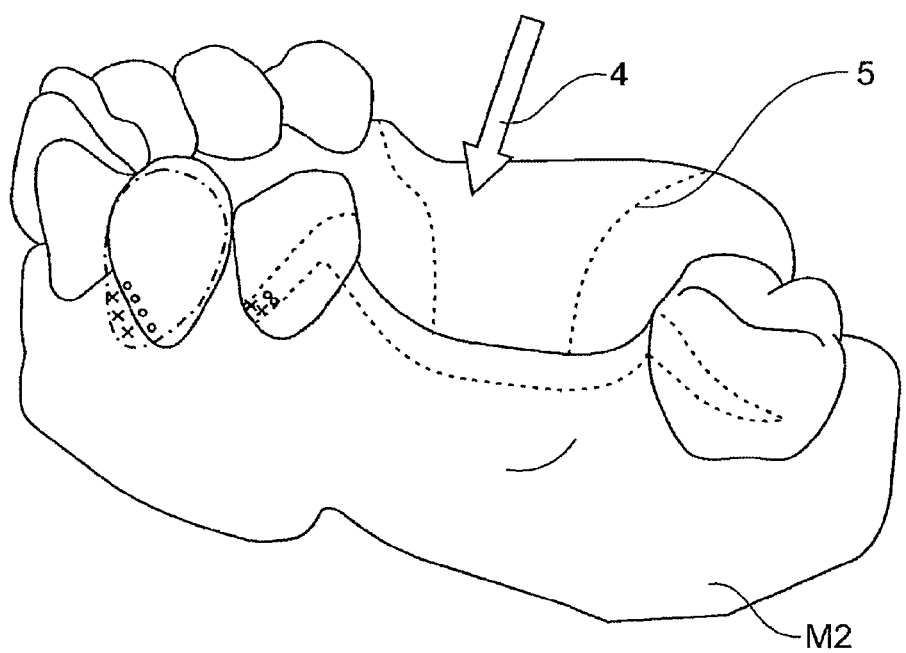

The undercut depths resulting from the proposed insertion axis 4 are determined on the basis of prosthesis model P, jaw model M2, and detected holding and support elements 3, and displayed in jaw model M2, e.g. by means of false colors. In FIG. 4, a contact surface 5 of the partial prosthesis is sketched on the jaw by means of a dotted line, which is determined on the basis of jaw model M1 and prosthesis reference model M1 or prosthesis model P. The undercut depths are indicated by crosses and circles. The undercut depths are determined in the area of contact surface 5 of the partial prosthesis, in particular in the areas of holding and support elements 3.

In addition to the marking and/or automatic detection of current holding and support elements 3, in another method step, areas within jaw model M2 may be automatically selected and/or selected by the user (dotted dashed line in FIG. 4) for which undercut depths are subsequently determined and displayed. Thus, undercut depths for areas of the jaw, on which new holding and support elements are to be placed, may be determined and may be taken into account in the placement of new holding and support elements.

This method step may be carried out prior to and/or after the calculation of the insertion axis.

If areas for holding and support elements to be added or other parts to be added are already fixed prior to the calculation of insertion axis 4 and are already previously marked in the jaw model, then these areas may be considered as additional holding support elements during the calculation of insertion axis 4 and the result may thus be improved.

By means of an input means, the potential may be provided to the user to change the proposed insertion axis 4, wherein all displayed undercut depths within jaw model M2 are automatically adapted to the changes.

In addition, in another optional method step, areas in the jaw which may cause possible wedging may be determined on the basis of prosthesis model P, jaw model M2, and insertion axis 4, and displayed in jaw model M2 (not shown). If lower side 2 of prosthesis model P is supplemented by the information from the third 3D model M3, then these areas are clearly identifiable. Without such an additional scan, at least probabilities may be determined and corresponding warnings may be displayed.

In a subsequent method step, jaw model M1 is blocked out. All undercut areas in jaw model M1 resulting from insertion axis 4 are filled in and the filling is subsequently removed again in the contact areas of the holding and support elements. Since the contact areas of the holding and support elements are already known, it is also possible to save these areas during the blocking out. A small inclination angle of e.g. 2° to 8° is used during blocking out.

In a subsequent design step, prosthesis model P is placed on blocked out jaw model M1, and changes or additions are carried out on prosthesis model P by the user by means of an input means, e.g. holding and support elements 3 and/or retention plates and overlapping areas for fixing are added and/or changed, wherein the effects of the changes are displayed with respect to undercut depths and/or wedgings for monitoring on blocked out jaw model M2.

If the additions to prosthesis model P are completed, then the added parts may subsequently be generated, for example, by means of a CAM device, on the basis of the current digital data and be fixed on the partial prosthesis, for example, by soldering the overlapping areas.

REFERENCES

1 Upper side of the prosthesis model
2 Lower side of the prosthesis model
3 Holding and support elements
4 Insertion axis
5 Contact surface of the partial prosthesis
M1 Prosthesis reference model
M2 Jaw model

The invention claimed is:
1. A method for computer-aided planning of a repair or adjustment of a dental partial prosthesis comprising the following method steps:
  a) generation of a first digital 3D model of a jaw with the partial prosthesis positioned on the jaw as a prosthesis reference model (M1),
  b) generation of a second digital 3D model of the jaw without the partial prosthesis as a jaw model (M2),
  c) determination of a positional relationship of the prosthesis reference model (M1) to the jaw model (M2),
  d) generation of a digital prosthesis model (P) by subtracting the jaw model (M2) from the prosthesis reference model (M2) while taking the positional relationship into account,
  e) automatic identification, or identification carried out by a user, of holding and/or support elements in the prosthesis model (P), f) calculation of an insertion axis of the partial prosthesis on the basis of the prosthesis model (P), g) calculation of undercut depths of the holding and/or support elements, resulting from the insertion axis, in the prosthesis model (P), h) display of the insertion axis and the undercut depths in a presentation of a jaw model (M2).

2. The method according to claim 1, wherein the proposed insertion axis is changed by the user by means of input means, and undercut depths displayed in the jaw model (M2) are automatically recalculated.

3. The method according to claim 1, wherein the jaw model (M2) is blocked out by taking the insertion axis into account, the prosthesis model (P) is placed on the blocked out jaw model (M2), and the prosthesis model (P) is supplemented and/or changed by a user by means of input means.

4. The method according to claim 1, wherein a third digital 3D model of a lower side of the partial prosthesis is generated and a lower side of the prosthesis model (P) is supplemented and/or replaced by the third digital 3D model.

5. The method according to claim 1, wherein prior to and/or after calculating the insertion axis and the undercut depths, areas to be monitored are automatically marked and/or marked by means of input means in the jaw model (M2), and undercut depths are calculated for these areas and are displayed in the jaw model (M2).

6. The method according to claim 1, wherein areas for holding and support elements to be added are marked on the jaw model (M2) prior to the calculation of the insertion axis and are taken into account during the calculation of the insertion axis.

7. The method according to claim 1, wherein the undercut depths are visualized by coloring the surface of the jaw model (M2) in false colors.

8. The method according to claim 1, wherein areas which might cause wedging are determined on the basis of the prosthesis model (P), the jaw model (M2), and the insertion axis, and are displayed in the jaw model (M2).

* * * * *